United States Patent [19]
Andresen et al.

[11] Patent Number: 5,768,330
[45] Date of Patent: *Jun. 16, 1998

[54] CO-DEPOSITION OF PALLADIUM DURING OXIDE FILM GROWTH IN HIGH-TEMPERATURE WATER TO MITIGATE STRESS CORROSION CRACKING

[75] Inventors: Peter Louis Andresen, Schenectady, N.Y.; Samson Hettiarachchi, Menlo Park, Calif.; Young Jin Kim, Clifton Park, N.Y.; Thomas Pompilio Diaz, San Martin, Calif.

[73] Assignee: General Electric Company, Schenectady, N.Y.

[*] Notice: The term of this patent shall not extend beyond the expiration date of Pat. No. 5,581,588.

[21] Appl. No.: 729,024

[22] Filed: Oct. 10, 1996

Related U.S. Application Data

[60] Division of Ser. No. 322,253, Oct. 13, 1994, Pat. No. 5,608,766, which is a continuation-in-part of Ser. No. 265,598, Jun. 24, 1994, abandoned, Ser. No. 209,175, Mar. 10, 1994, abandoned, Ser. No. 143,513, Oct. 29, 1993, abandoned, and Ser. No. 143,514, Oct. 29, 1993, Pat. No. 5,448,605.

[51] Int. Cl.$^6$ .................................................. G21C 9/00
[52] U.S. Cl. .......................... 376/305; 376/301; 376/306; 422/11; 422/14; 422/19
[58] Field of Search ................................ 376/301, 305, 376/306, 356, 357; 422/11, 14, 19

[56] References Cited

U.S. PATENT DOCUMENTS

| | | | |
|---|---|---|---|
| 3,923,688 | 12/1975 | Hammel et al. | 252/432 |
| 4,093,559 | 6/1978 | Fernholz et al. | 252/443 |
| 4,479,892 | 10/1984 | Shibata | 252/514 |
| 4,828,790 | 5/1989 | Honda et al. | 376/306 |
| 4,889,772 | 12/1989 | Bergmann et al. | 428/547 |
| 5,028,384 | 7/1991 | Skarpelos et al. | 376/306 |

(List continued on next page.)

FOREIGN PATENT DOCUMENTS

| | | |
|---|---|---|
| 0265723 | 5/1988 | European Pat. Off. |
| 0450440 | 9/1991 | European Pat. Off. |
| 0450444 | 9/1991 | European Pat. Off. |
| 0514089 | 11/1992 | European Pat. Off. |
| 0526160 | 2/1993 | European Pat. Off. |
| 0 540 201 A2 | 5/1993 | European Pat. Off. |
| 0 651 073 A1 | 5/1995 | European Pat. Off. |
| 0 651 397 A1 | 5/1995 | European Pat. Off. |
| 0 671 485 A1 | 9/1995 | European Pat. Off. |
| 9218665 | 10/1992 | WIPO . |

OTHER PUBLICATIONS

Derwent Publications Ltd., London, GB; AN 84–059353 & JP-A-50 016 983 (Katayama Kagaku Kogyo Kenkyushi). Abstract, no date available.

Kowalczyk et al. "Characterization of palladium . . . " 3rd Symp. On Chem. Perspectives of Microelectronics Material, Boston, USA, Nov. 30–Dec. 3, 1992, Mat. Res. Soc. Symp. Proc. vol. 282, pp. 353–358.

Patent Abstracts of Japan, vol. 013 No. 505 (P–959) 14 Nov. 1989. Abstract.

Database WPI, Section CH, Week 8519, Derwent Publications Ltd. London, GB, 27 Mar. 1985. Abstract.

Primary Examiner—Kathryn L. Gorgos
Assistant Examiner—Chrisman D. Carroll
Attorney, Agent, or Firm—Nixon & Vanderhye

[57] ABSTRACT

A method for improving the performance and longevity of coatings of metal deposited from aqueous solutions of inorganic, organic or oraganometallic metal compounds. The method involves co-deposition of noble metal or corrosion-inhibiting non-noble metal during growth of oxide film on a component made of alloy, e.g., stainless steels and nickel-based alloys. The result is a metal-doped oxide film having a relatively longer life in the reactor operating environment. In particular, incorporation of palladium into the film provides greatly increased catalytic life as compared to palladium coatings which lie on the oxide surface.

2 Claims, 5 Drawing Sheets

U.S. PATENT DOCUMENTS

| | | | |
|---|---|---|---|
| 5,130,080 | 7/1992 | Niedrach | 376/305 |
| 5,130,081 | 7/1992 | Niedroch | 376/305 |
| 5,135,709 | 8/1992 | Andresen et al. | 376/305 |
| 5,164,152 | 11/1992 | Kim et al. | 376/305 |
| 5,198,154 | 3/1993 | Yokoyama et al. | 252/514 |
| 5,245,642 | 9/1993 | Lin | 376/310 |
| 5,267,289 | 11/1993 | Bryan | 376/414 |
| 5,317,610 | 5/1994 | Kita et al. | 376/414 |
| 5,321,730 | 6/1994 | Eckardt | 376/301 |
| 5,360,673 | 11/1994 | Mayer et al. | 428/546 |
| 5,377,245 | 12/1994 | Uetake et al. | 376/305 |
| 5,581,588 | 12/1996 | Andressen et al. | 376/305 |

5,768,330

1

CO-DEPOSITION OF PALLADIUM DURING OXIDE FILM GROWTH IN HIGH-TEMPERATURE WATER TO MITIGATE STRESS CORROSION CRACKING

RELATED PATENT APPLICATIONS

This application is a Rule 60 divisional of U.S. patent application Ser. No. 08/322,253, filed Oct. 13, 1994, now U.S. Pat. No. 5,608,766, which is a continuation-in-part of each of the following U.S. Pat. applications: Ser. No. 08/265,598, filed Jun. 24, 1994, now abandoned; Ser. No. 08/209,175, filed Mar. 10, 1994, now abandoned; Ser. No. 08/143,513, filed Oct. 29, 1993, now abandoned; and Ser. No.08/143,514, filed Oct. 29, 1993, now U.S. Pat. No. 5,448,605.

FIELD OF THE INVENTION

This invention relates to reducing the corrosion potential of components exposed to high-temperature water. As used herein, the term "high-temperature water" means water having a temperature of about 150° C. or greater, steam, or the condensate thereof. High-temperature water can be found in a variety of known apparatus, such as water deaerators, nuclear reactors, and steam-driven power plants.

BACKGROUND OF THE INVENTION

A light-water nuclear reactor has a core of nuclear fuel which is cooled by recirculating water. A reactor pressure vessel contains the reactor coolant. Piping circuits carry the heated water or steam to the steam generators or turbines and carry circulated water or feedwater back to the vessel. Operating pressures and temperatures for the reactor pressure vessel are about 7 MPa and 288° C. for a boiling water reactor (BWR), and about 15 MPa and 320° C. for a pressurized water reactor (PWR). The materials used in both BWRs and PWRs must withstand various loading, environmental and radiation conditions.

Some of the materials exposed to high-temperature water include carbon steel, alloy steel, stainless steel, and nickel-based, cobalt-based and zirconium-based alloys. Despite careful selection and treatment of these materials for use in water reactors, corrosion occurs on the materials exposed to the high-temperature water. Such corrosion contributes to a variety of problems, e.g., stress corrosion cracking, crevice corrosion, erosion corrosion, sticking of pressure relief valves and buildup of the gamma radiation-emitting Co-60 isotope.

Stress corrosion cracking (SCC) is a known phenomenon occurring in reactor components, such as structural members, piping, fasteners, and welds, exposed to high-temperature water. As used herein, SCC refers to cracking propagated by static or dynamic tensile stressing in combination with corrosion at the crack tip. The reactor components are subject to a variety of stresses associated with, e.g., differences in thermal expansion, the operating pressure needed for the containment of the reactor cooling water, and other sources such as residual stress from welding, cold working and other asymmetric metal treatments. In addition, water chemistry, welding, heat treatment, and radiation can increase the susceptibility of metal in a component to SCC.

It is well known that SCC occurs at higher rates when oxygen is present in the reactor water in concentrations of about 5 ppb or greater. SCC is further increased in a high radiation flux where oxidizing species, such as oxygen, hydrogen peroxide, and short-lived radicals, are produced from radiolytic decomposition of the reactor water. Such oxidizing species increase the electrochemical corrosion potential (ECP) of metals. Electrochemical corrosion is caused by a flow of electrons from anodic to cathodic areas on metallic surfaces. The ECP is a measure of the thermodynamic tendency for corrosion phenomena to occur, and is a fundamental parameter in determining rates of, e.g., SCC, corrosion fatigue, corrosion film thickening, and general corrosion.

In a BWR, the radiolysis of the primary water coolant in the reactor core causes the net decomposition of a small fraction of the water to the chemical products $H_2$, $H_2O_2$, $O_2$ and oxidizing and reducing radicals. For steady-state operating conditions, equilibrium concentrations of $O_2$, $H_2O_2$, and $H_2$ are established in both the water which is recirculated and the steam going to the turbine. These concentrations of $O_2$, $H_2O_2$ and $H_2$ can result in conditions that promote intergranular stress corrosion cracking (IGSCC) of susceptible materials of construction.

As used herein, the term "critical potential" means a corrosion potential at or below a range of values of about −230 to −300 mV based on the standard hydrogen electrode (SHE) scale. IGSCC proceeds at an accelerated rate in systems in which the ECP is above the critical potential, and at a substantially lower or zero rate in systems in which the ECP is below the critical potential. Water containing oxidizing species such as oxygen and hydrogen peroxide increase the ECP of metals exposed to the water above the critical potential, whereas water with little or no oxidizing species present results in an ECP below the critical potential.

Thus, susceptibility to SCC in BWRs is highly influenced by corrosion potential. FIG. 1 shows the observed and predicted crack growth rate as a function of corrosion potential for furnace-sensitized Type 304 stainless steel at 27.5 to 30 MPa$\sqrt{m}$ in 288° C. water over the range of solution conductivities from 0.1 to 0.5 μS/cm. Data points at elevated corrosion potentials and growth rates correspond to irradiated water chemistry conditions in test or commercial reactors. Reduction of the corrosion potential is the most widely pursued approach for mitigating SCC in existing plants.

One method employed to mitigate IGSCC of susceptible material is the application of hydrogen water chemistry (HWC), whereby the oxidizing nature of the BWR environment is modified to a more reducing condition. This effect is achieved by adding hydrogen gas to the reactor feedwater. When the hydrogen reaches the reactor vessel, it reacts with the radiolytically formed oxidizing species on metal surfaces to reform water, thereby lowering the concentration of dissolved oxidizing species in the water in the vicinity of metal surfaces. The rate of these recombination reactions is dependent on local radiation fields, water flow rates and other variables.

The injected hydrogen reduces the level of oxidizing species in the water, such as dissolved oxygen, and as a result lowers the ECP of metals in the water. However, factors such as variations in water flow rates and the time or intensity of exposure to neutron or gamma radiation result in the production of oxidizing species at different levels in different reactors. Thus, varying amounts of hydrogen have been required to reduce the level of oxidizing species sufficiently to maintain the ECP below the critical potential required for protection from IGSCC in high-temperature water.

It has been shown that IGSCC of Type 304 stainless steel used in BWRs can be mitigated by reducing the ECP of the stainless steel to values below −0.230 V(SHE). However, high hydrogen additions, e.g., of about 200 ppb or greater, that may be required to reduce the ECP below the critical potential, can result in a higher radiation level in the steam-driven turbine section from incorporation of the short-lived N-16 species in the steam.

Thus, recent investigations have focused on using minimum levels of hydrogen to achieve the benefits of HWC with minimum increase in the main steam radiation dose rates.

An effective approach to achieve this goal is to either coat or alloy the stainless steel surface with palladium or any other platinum group metal. As used herein, the term "platinum group metal" means metals from the group consisting of platinum, palladium, osmium, ruthenium, iridium, rhodium, and mixtures thereof. The presence of palladium on the stainless steel surface reduces the hydrogen demand to reach the required IGSCC critical potential of −0.230 V(SHE). Compared to the HWC technique, which employs large hydrogen additions to suppress and recombine oxygen and hydrogen peroxide formed by radiolysis to very low levels (e.g., <2 ppb), the noble metal approach requires only that sufficient hydrogen be present so that, as water is formed on the catalytic surface, all oxygen and hydrogen peroxide are consumed (e.g., $2H_2 + O_2 \rightarrow 2H_2O$). Additionally, lower potentials (generally the thermodynamic minimum) are obtained. Depending on the precise location within a BWR, the hydrogen addition required in the noble metal approach is reduced by a factor of 5 to 100.

The fundamental importance of corrosion potential versus, e.g., the dissolved oxygen concentration per se is shown in FIG. 2, where the crack growth rate of a crack growth specimen coated with palladium by electroless plating drops dramatically once excess hydrogen conditions are achieved, despite the presence of a relatively high oxygen concentration. FIG. 2 shows plots of crack length and corrosion potential vs. time for a Pd-coated crack growth specimen of sensitized Type 304 stainless steel showing accelerated crack growth in 288° C. water containing excess oxygen (e.g., 1000 ppb $O_2$ and 48 ppb $H_2$). Because the crack growth specimen was Pd-coated, the change to excess hydrogen (e.g., 400 ppb $O_2$ and 78 ppb $H_2$) caused the corrosion potential and crack growth rate to drop.

U.S. Pat. No. 5,135,709 to Andresen et al. discloses a method for lowering the ECP on components formed from carbon steel, alloy steel, stainless steel, nickel-based alloys or cobalt-based alloys which are exposed to high-temperature water by forming the component to have a catalytic layer of a platinum group metal. This layer catalyzes the recombination of reducing species, such as hydrogen, with oxidizing species, such as oxygen or hydrogen peroxide, that are present in the water of a BWR. Such catalytic action at the surface of the alloy can lower the ECP of the alloy below the critical potential where IGSCC is minimized. As a result, the efficacy of hydrogen additions to high-temperature water in lowering the ECP of components made from the alloy and exposed to the injected water is increased manyfold. Furthermore, it is possible to provide catalytic activity at metal alloy surfaces if the metal substrate of such surfaces contains a catalytic layer of a platinum group metal. A solute can be provided by methods known in the art, for example by addition to a melt of the alloy or by surface alloying. Alternatively, a coating of platinum group metal provides a catalytic layer and catalytic activity at the surface of the metal. Suitable coatings can be deposited by methods well known in the art, such as plasma spraying, flame spraying, chemical vapor deposition, physical vapor deposition processes such as sputtering, welding such as metal inert gas welding, electroless plating, and electrolytic plating. However, these approaches are ex-situ techniques in that they cannot be practiced while the reactor is in operation.

The development of techniques to apply palladium in situ to all wetted components represents a breakthrough in extending the applications of the noble metal technology, since manual application (e.g., by thermal spray or fusion cladding) requires complex tooling, is slow and expensive, and can only coat surfaces to which there is sufficiently good access. U.S. patent applications Ser. Nos. 08/143,513, now abandoned, and 08/209,175, now abandoned, disclose a technique to coat or dope oxidized stainless steel surfaces in situ by injecting a metal-containing compound into the high-temperature water, which metal has the property of improving the corrosion resistance of those surfaces. The compound is injected in situ in the form of a solution or a suspension. The preferred compound for this purpose is palladium acetylacetonate, an organometallic compound. The concentration of palladium in the reactor water is preferably in the range of 5 to 100 ppb. Upon injection, the palladium acetylacetonate decomposes and deposits palladium on the oxidized surface. Palladium may be deposited within or on the surface of the oxide film in the form of a finely divided metal. The oxide film is believed to include mixed nickel, iron and chromium oxides.

The ECPs of the stainless steel components should all drop by ~300 mV after palladium injection. It is possible to reduce the ECP of Type 304 stainless steel to IGSCC protection values without injecting hydrogen provided that organics are present in the water. This occurs because of the catalytic oxidation of organics on Pd-doped surfaces.

Following palladium injection, hydrogen can be injected into the reactor water. As hydrogen is added, the potential of the Pd-doped oxide film on the stainless steel components is reduced to values which are much more negative than when hydrogen is injected into a BWR having stainless steel components which are not doped with palladium.

Other palladium compounds of organic, organometallic or inorganic nature, as well as compounds of other platinum group metals or non-platinum group metals such as titanium and zirconium, can also be used.

In summary, the oxygen content of the reactor water can be reduced by palladium injection alone initially. Some oxygen will be reduced by the organics of the organometallic palladium compound following thermal decomposition or radiolytic decomposition (induced by gamma and neutron radiation) of the organometallic palladium compound. When palladium injection is combined with hydrogen injection, oxygen will also be reduced as a result of the recombination of dissolved oxygen and hydrogen molecules at the Pd-doped surfaces forming water molecules.

The effectiveness of alloys or coatings that contain at least about 0.1% noble metal (which category of metals is also referred to in the art as "platinum group metals") has been extensively demonstrated. The data presented in FIG. 3 were obtained using pre-oxidized Type 304 stainless steel electrodes held in 288° C. water containing 300 ppb $O_2$ for 8 months. The presence of platinum reduced the corrosion potential of Type 304 stainless steel for dissolved hydrogen levels in excess of about 24 ppb. The amount of platinum was varied as follows: (•) no Pt; (♦) 0.1% Pt; (▲) 0.35% Pt; (■) 1.0% Pt; (○) pure Pt.

In situ palladium deposition from aqueous solutions on pre-oxidized materials has also been shown to be effective, both in terms of deposition (the presence of palladium on the surface has been confirmed by Auger electron spectroscopy and X-ray photoelectron spectroscopy) and catalytic response (in high-temperature water containing stoichiometric excess hydrogen). FIG. 4 shows a plot of crack length and solution conductivity vs. time for a Pd-coated crack growth specimen of furnace-sensitized Type 304 stainless steel showing accelerated crack growth in 288° C. water containing about 180 ppb $O_2$ and 9.6 ppb $H_2$. Because the crack growth specimen was Pd-coated (i.e., in shallow water by the high-velocity oxy-fuel technique with Type 309L stainless steel +0.42% Pd), the change to excess hydrogen (i.e., 150 ppb $O_2$ and 24 ppb $H_2$) caused the corrosion potential and crack growth rate to drop.

FIG. 5 is a plot of crack length vs. time for a Pd-doped crack growth specimen of furnace-sensitized Alloy 182 weld metal showing accelerated crack growth in 288° C. water containing excess oxygen and reduced crack growth under excess hydrogen conditions in the presence of palladium. Palladium doping was performed on a pre-oxidized (and previously tested) crack growth specimen from a 100 ppb (as Pd) aqueous solution of palladium acetylacetonate. The specimen was first exposed to zinc and then Pd-doped for 48 hr.

However, it has also been shown that exposure to prolonged ultrasonic cleaning significantly reduces both the presence of palladium and the surface catalytic response. FIG. 6 shows a significant reduction in the catalytic effectiveness of in-situ palladium deposition in reducing the corrosion potential in 288° C. water under stoichiometric excess hydrogen conditions following prolonged exposure to ultrasonic cleaning. Deposition was performed on a pre-oxidized coupon specimen from a 100 ppb (as Pd) aqueous solution of palladium acetylacetonate. FIG. 6 shows corrosion potential as a function of $H_2/O_2$ molar ratio for the following materials in 288° C. water having 1.0 ppm $O_2$: (•) undoped Type 304 stainless steel; (▲) Pd-doped Type 304 stainless steels doped by in situ deposition and not exposed to ultrasonic cleaning; (■) Pd-doped Type 304 stainless steels doped by in situ deposition and then exposed to 60° C. water for 1 week in an ultrasonic bath; and (○) pure platinum. The Pd-doped specimen showed a 250 mV increase in ECP after being exposed to ultrasonic cleaning. These results indicate the loss of the surface catalytic property.

SUMMARY OF THE INVENTION

The present invention is a method for improving the performance and longevity of coatings of noble metal or any other metal deposited from aqueous solutions of inorganic, organic or oraganometallic compounds. In particular, the invention is a method of distributing a desired metal throughout the thickness of an oxide film formed on nuclear reactor components. The method of the invention optionally includes the step of removing some or all of the oxide film on the surface of a reactor component in situ and then co-depositing metal, e.g., palladium, during subsequent growth of the oxide film. In cases where the deposited metal is a noble metal, e.g., palladium, the result of this technique is a noble metal-doped oxide film having a relatively longer catalytic life in the reactor operating environment.

The concept of the present invention involves preparation by environmental, mechanical or decontamination exposure of a pre-oxidized metal surface and/or exposure to aqueous metal compounds during subsequent oxide film growth to incorporate the metal, e.g., palladium or zirconium, into the oxide film. Incorporation of palladium or zirconium into the film provides greatly increased longevity of the corrosion inhibition effect as compared to palladium or zirconium coatings which lie on the oxide surface or penetrate only a thin stratum at the oxide surface.

DETAILED DESCRIPTION OF THE PREFERRED EMBODIMENTS

Figure 1:
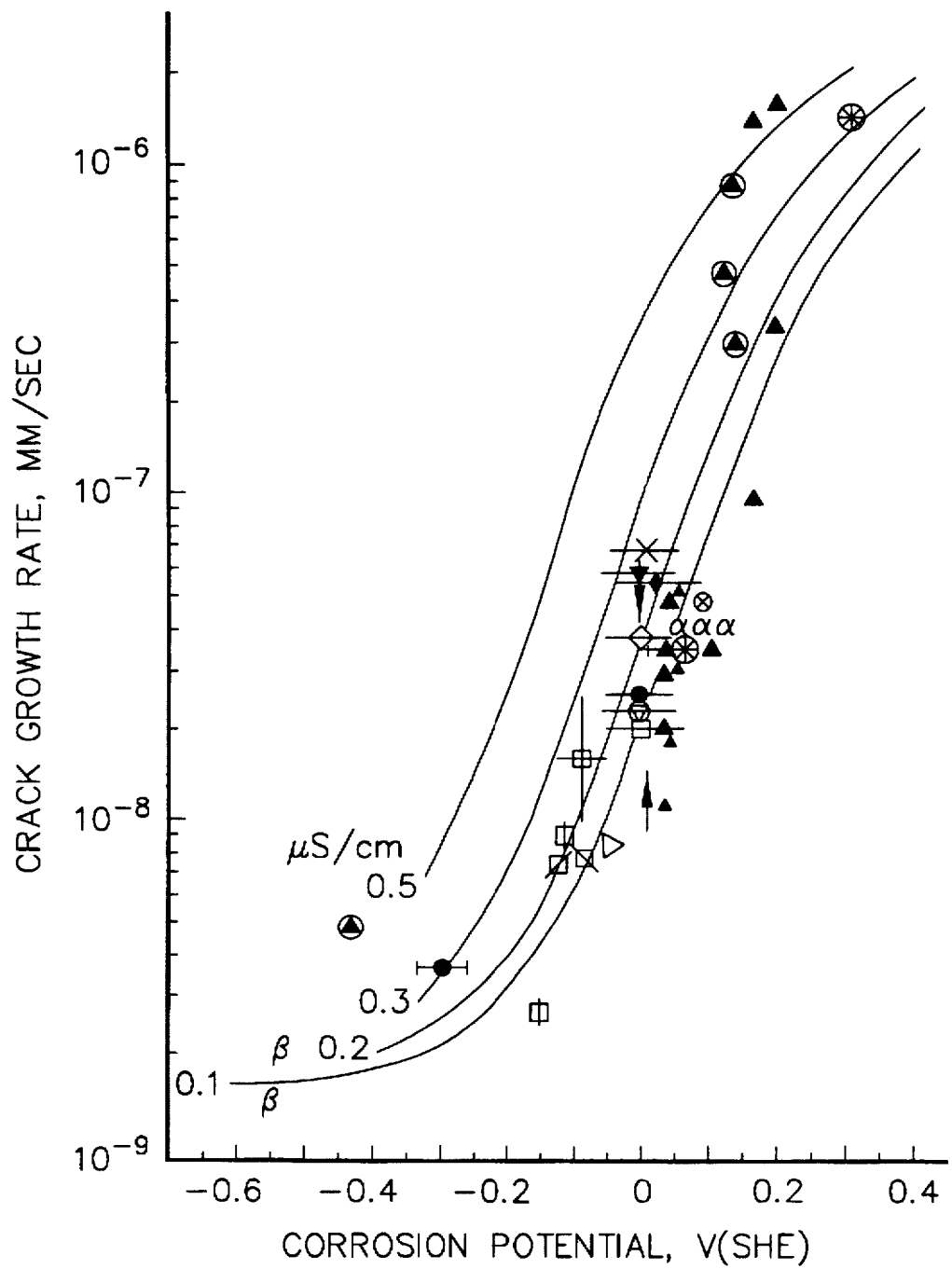
FIG. 1 shows the observed and predicted crack growth rate as a function of corrosion potential for furnace-sensitized Type 304 stainless steel in 288° C. water over the range of solution conductivities of 0.1–0.5 µS/cm.
Figure 2:
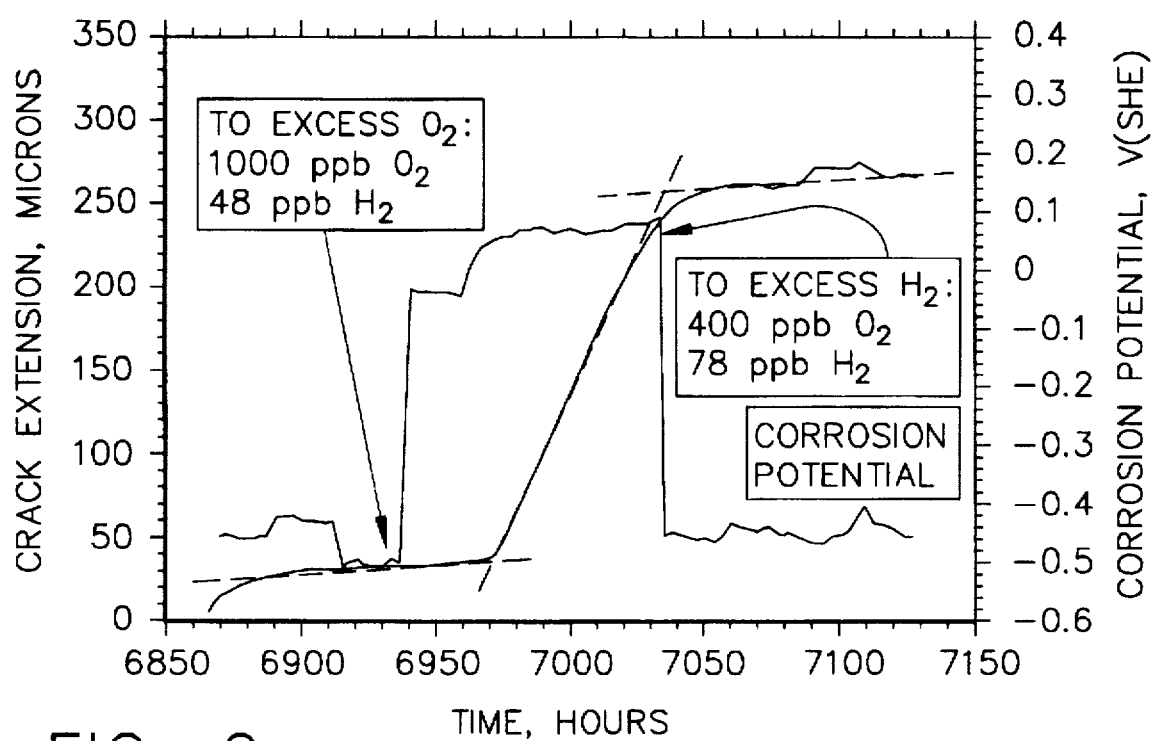
FIG. 2 shows plots of crack length and corrosion potential vs. time for a Pd-coated crack growth specimen of sensitized Type 304 stainless steel in 288° C. water for excess oxygen and excess hydrogen conditions.

The preferred embodiment of the present invention is a technique to dope stainless steel surfaces with palladium in situ by injecting a palladium-containing compound into the high-temperature water of a BWR while oxide film is forming on the stainless steel surface. Preferably the palladium compound is injected in the form of a solution or suspension at a point upstream of the feedwater inlet. The high temperatures as well as the gamma and neutron radiation in the reactor core act to decompose the compound, thereby freeing palladium species for incorporation in the oxide film as its grows. As used herein, the term "species" means ions or atoms. One Pd-containing compound successfully used for this purpose is an organometallic compound, palladium acetylacetonate. However, other noble metal compounds of organic, organometallic and inorganic nature can also be used for this purpose. The palladium acetylacetonate compound is dissolved in an ethanol/water mixture or in water alone to form a solution or suspension which is injected into the reactor coolant.

The palladium gets incorporated into the stainless steel oxide film via a thermal decomposition process of the organometallic compound. As a result of that decomposition, Pd species become available to replace atoms, e.g., Fe atoms, in the oxide film, thereby producing a Pd-doped oxide film on stainless steel.

The method of the present invention involves in situ removal of some or all of the oxide film from the surfaces of wetted reactor component and co-deposition of noble metal during subsequent growth of oxide film on the same wetted surfaces. The result is a noble metal-doped oxide film having a relatively longer catalytic life in the reactor operating environment. Incorporation of palladium into the film provides greatly increased catalytic life as compared to palladium coatings which lie on the oxide surface.

In accordance with the broad concept of the present invention, several approaches are possible. In the simplest approach, mechanical cleaning (e.g., by flapper wheel or ultra-high-pressure water jet) is used to remove most or all of the oxide film from the reactor component to be treated. Because the oxide film formed on a reactor component reaches a limiting thickness, some portion of the oxide film must be removed before more oxide film, which forms the matrix for the metal dopant, can be grown. After removal of some oxide film, the appropriate aqueous noble metal compound is added to the reactor water prior to initial heat up. This can be accomplished without the nuclear fuel being present by using the recirculation pumps. As the oxide film reforms, palladium will be incorporated into the film. While it is desirable to use the highest possible palladium concentrations consistent with plant and cost considerations, levels in the preferred range of 5 to 100 ppb Pd should be sufficient.

In accordance with the preferred method, after the oxide film has been thinned, noble metal doping of newly formed oxide film can be performed at regular intervals to produce a noble metal concentration which varies cyclically in the thickness direction or can be performed continuously to produce a noble metal concentration which is generally constant in the thickness direction.

Since mechanical cleaning is expensive, complex and limited to reactor components that are readily accessible, more attractive approaches for preparing the oxidized alloy surfaces include chemical decontamination (which is periodically performed in many plants to reduce the radioactivity, e.g., of piping from $Co^{60}$ and other elements which incorporate into the oxide) and exposure to hydrogen water chemistry, which will thin the existing oxide film. Additions of zinc will also reduce the oxide film thickness. However, it may be desirable to halt the zinc additions during the palladium doping process since zinc appears to densify the film. The formation of ZnO on alloy surfaces has been shown to yield many benefits in BWRs, including reduced incorporation of Co60 in films (thereby lowering the radiation level, e.g., in piping) and reduced susceptibility to SCC.

A further aspect of the present invention is that cycling the temperature during the palladium doping process (e.g., by repeatedly raising the water temperature to 550° F. and then cooling the water to 100° F.) should be beneficial, since the solubility of the metal oxides, film thickness and semiconducting properties of the oxide film change with change in temperature. This may be especially valuable following zinc exposure, since zinc desorbs from the oxide films at lower temperatures, providing more sites for the deposition of palladium and more opportunities for film growth.

The advantage of the method of the invention, in which the oxide film on alloy surfaces is removed or thinned before palladium deposition, is that palladium is distributed throughout the oxide film in the thickness direction. In contrast, when pre-oxidized alloy surfaces are treated with, e.g., palladium acetylacetonate, the palladium is deposited only on the surface of the oxide. If this deposited palladium is removed from the surface, e.g., by very high flow rates of the reactor coolant, the catalytic response of the surface coating with palladium is decreased, whereas in the case of co-deposition of palladium during oxide film growth, the catalytic response may be sustained due to the presence of palladium species throughout the thickness of the oxide film.

Cylindrical coupons of as-machined Type 304 stainless steel were exposed in 288° C. water containing about 300 ppb $O_2$ for 16 hr. Thereafter, the coupons were exposed in 288° C. water containing about 300 ppb $O_2$ and 100 ppb Pd as palladium acetylacetonate for 6–8 hours. This cycle was repeated six times. During palladium doping cycles, palladium acetylacetonate was injected. During oxidizing cycles, palladium acetylacetonate was not injected and the palladium acetylacetonate injected during the doping cycle had been removed by the water cleanup system. During the doping cycle, palladium deposits on the high-temperature oxide film and as this oxide films thickens over time, palladium is incorporated throughout the layer of oxide in the thickness direction. However, the palladium concentration in the thickness direction of the oxide film varies as a function of the amount of palladium in the solution in which the coupon is exposed.

Figure 7:
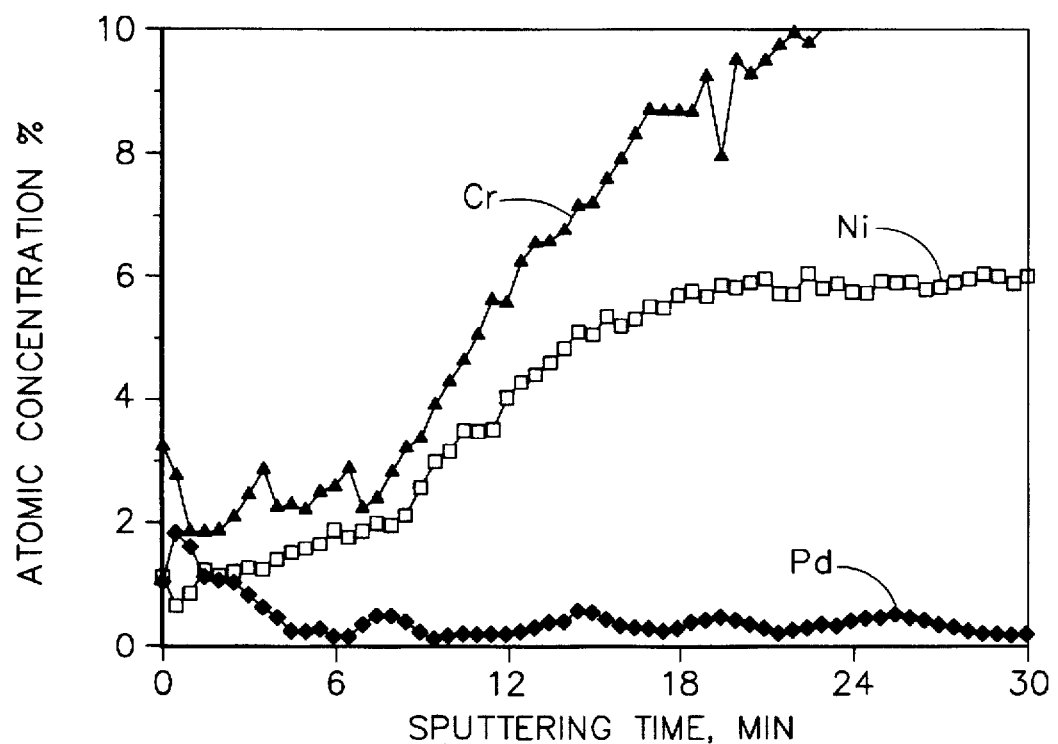
FIG. 7 is an Auger electron spectroscopy depth profile for Cr (▲), Ni (□) and Pd (♦) of the as-exposed surface of as-machined Type 304 stainless steel exposed in 288° C. water containing about 300 ppb $O_2$ and 100 ppb Pd as palladium acetylacetonate, palladium doped by the co-deposition technique.
Figure 3:
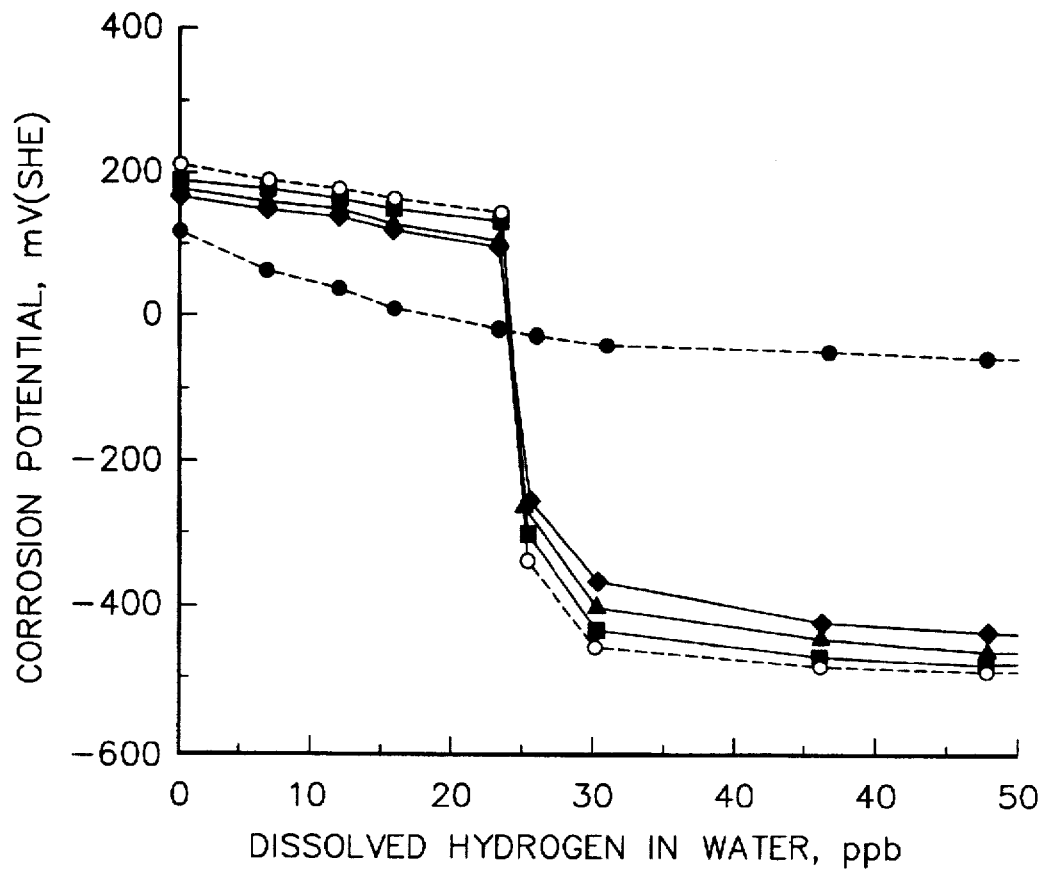
FIG. 3 is a plot showing the ECPs of platinum, Pt-doped Type 304 stainless steel containing various levels of platinum and undoped Type 304 stainless steels in 288° C. water containing 300 ppb $O_2$ as a function of the amount of dissolved hydrogen.
Figure 4:
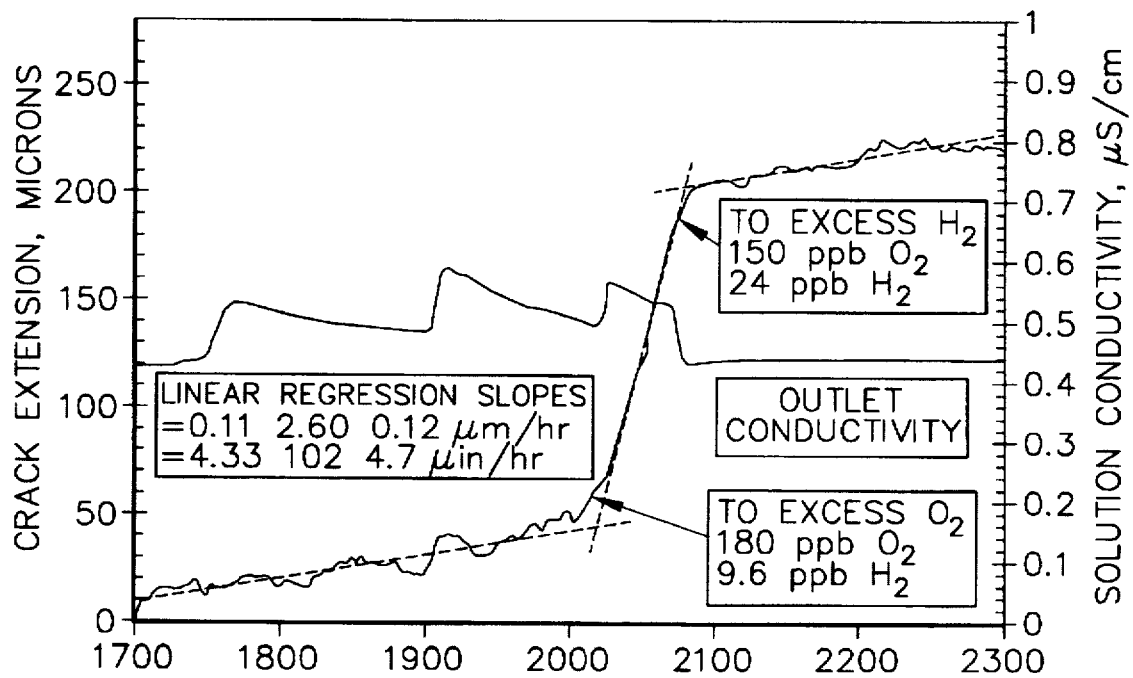
FIG. 4 shows plots of crack length and solution conductivity vs. time for a Pd-coated crack growth specimen of sensitized Type 304 stainless steel in 288° C. water for excess oxygen and excess hydrogen conditions. The Type 304 stainless steel was thermally sprayed by the hyper velocity oxy-fuel (HVOF) technique with a powder of Type 309L stainless steel containing 0.42% Pd.
Figure 5:
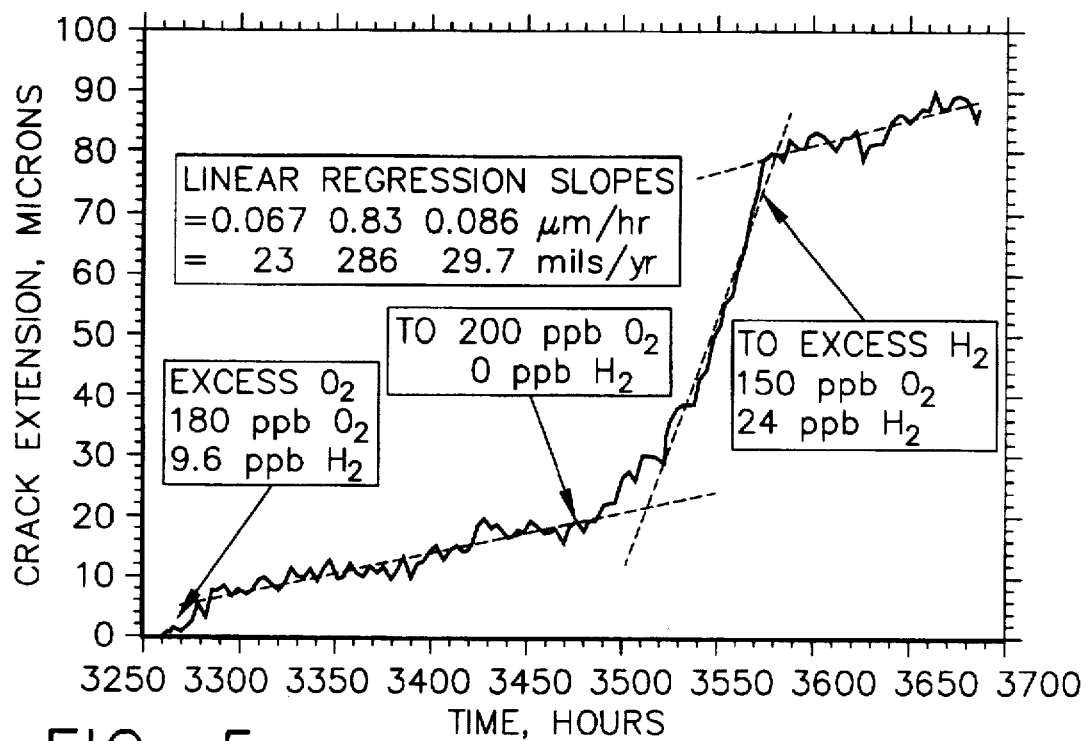
FIG. 5 is a plot of crack length vs. time for a Pd-doped crack growth specimen of furnace-sensitized Alloy 182 weld metal showing accelerated crack growth in 288° C. water containing excess oxygen and reduced crack growth under excess hydrogen conditions in the presence of palladium deposited in situ.
Figure 6:
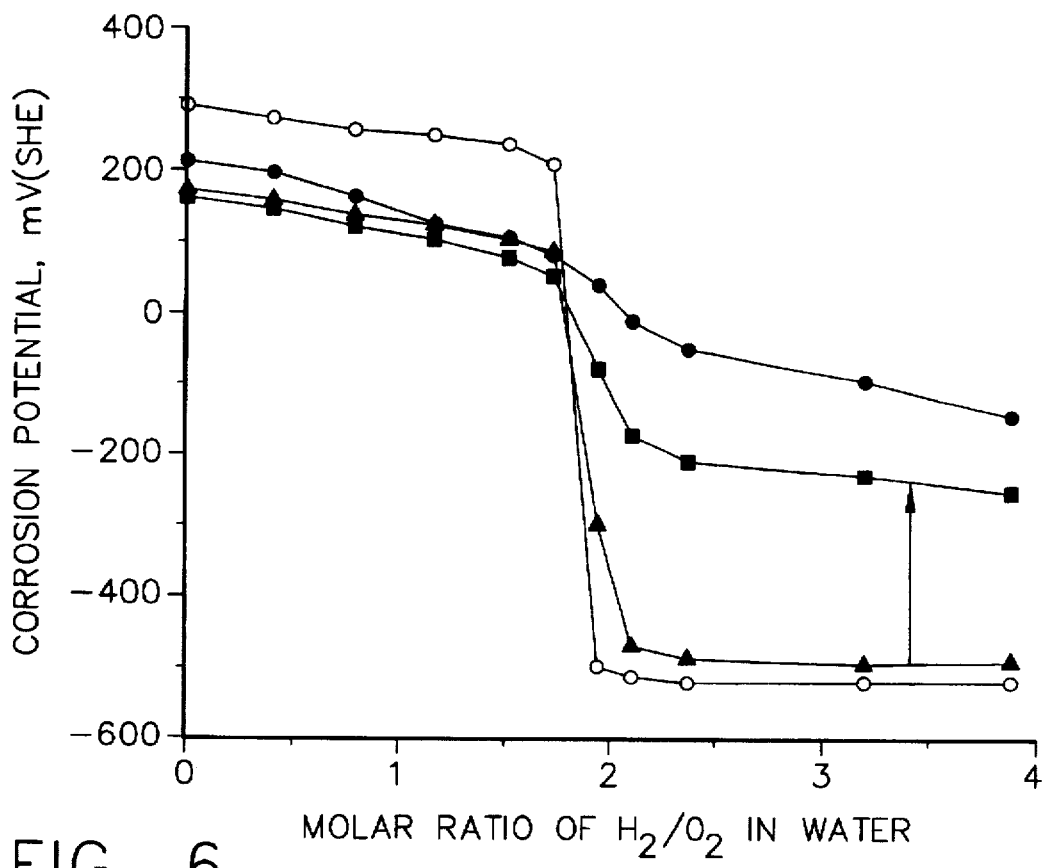
FIG. 6 is a plot showing the ECPs of undoped Type 304 stainless steel (•), Pd-doped Type 304 stainless steels doped by in situ deposition and not exposed to ultrasonic cleaning (▲), Pd-doped Type 304 stainless steels doped by in situ deposition and then exposed to ultrasonic cleaning (■), and pure platinum (○) in 288° C. water as a function of the $H_2/O_2$ molar ratio.
Figure 8:
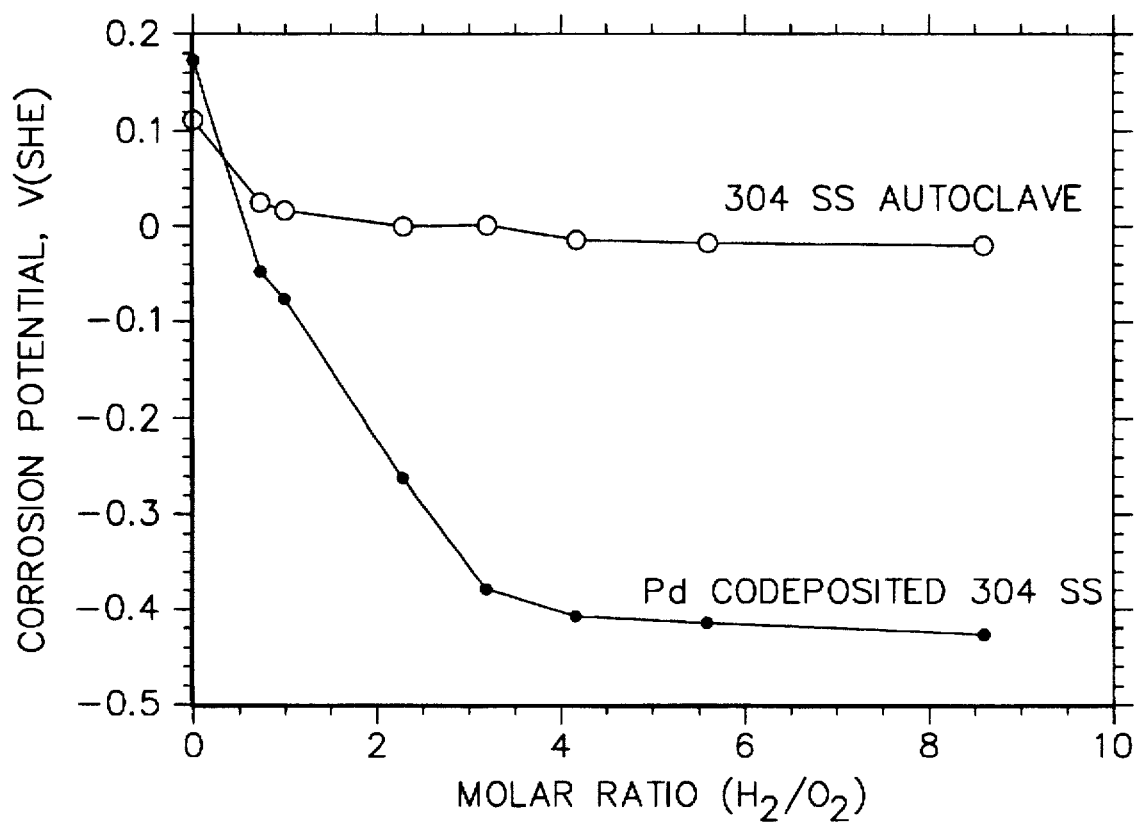
FIG. 8 is a plot showing the ECPs of a palladium co-deposited specimen of Type 304 stainless steel (•) and a Type 304 stainless steel autoclave (○) as a function of the $H_2/O_2$ molar ratio.

During this experiment, the incorporation of palladium was observed by depth profiling the Auger electron spectroscopy of the as-exposed surface. The cyclical variation of the palladium doping in the thickness direction can be seen in FIG. 7. The excellent corrosion potential response of this palladium co-deposited specimen is shown in FIG. 8 by the sharp decrease in corrosion potential at $H_2/O_2$ molar ratios in the range of about 1.5–2.

The method of the present invention can also be used to dope oxide films on reactor components with corrosion-inhibiting non-noble metal. In accordance with this method, the component or structural material is immersed in a solution or suspension of a compound containing the non-noble metal. The non-noble metal must have the property of increasing the corrosion resistance of the stainless steel or other metal surface when incorporated therein or deposited thereon. The selected compound must have the property that it decomposes under reactor thermal conditions to release species of the selected non-noble metal which incorporate in or deposit on the oxide film formed on the stainless steel or other metal surfaces. The non-noble metals which can be used are selected from the group consisting of zirconium, niobium, yttrium, tungsten, vanadium, titanium, molybdenum, chromium and nickel. The preferred compounds in accordance with the invention are those containing zirconium, e.g., the organometallic compounds zirconium acetylacetonate and inorganic compounds zirconium nitrate and zirconyl nitrate.

The present invention offers the advantage that alloy surfaces can be doped with palladium or other metal using an in-situ technique (while the reactor is operating) which is simple in application and also inexpensive. However, this technique can also be implemented for coating ex-situ components. In addition, the technique can be applied to operating BWRs and PWRs and their associated components, such as steam generators.

The foregoing method have been disclosed for the purpose of illustration. Variations and modifications of the disclosed method will be readily apparent to practitioners skilled in the art of mitigating stress corrosion cracking. For example, noble metals other than palladium can be applied using this technique. The noble metal can be injected in the form of an organic or inorganic compound in conjunction with injection of small amounts of hydrogen to reduce the potential of stainless steel reactor components. One option is to inject the palladium acetylacetonate solution or suspension via the same port by which dissolved hydrogen is injected. The corrosion-inhibiting non-noble metals can be used even in the absence of hydrogen injection. In addition, the doping technique of the invention is not restricted to use with stainless steel surfaces, but also has application in reducing the ECP of other metals which are susceptible to IGSCC, e.g., nickel-based alloys. All such variations and modifications are intended to be encompassed by the claims set forth hereinafter.

We claim:

1. A nuclear reactor component made of an alloy and having an oxide film formed on its surface, wherein said oxide film has incorporated therein a species of a metal having the property of increasing the corrosion resistance of said alloy when incorporated in said oxide film, said metal species being a noble metal or a non-noble metal selected from the group consisting of zirconium, niobium, yttrium, tungsten, vanadium, titanium and molybdenum, said metal species having a concentration throughout the oxide film sufficient to reduce the corrosion potential at the surface of said oxide film to below a critical potential conducive to stress corrosion cracking even as the surface of said oxide film is gradually removed and a new surface is exposed.

2. An alloy component as defined in claim 1 wherein said metal species is a noble metal.

* * * * *